United States Patent [19]

Yoneda et al.

[11] 4,294,832
[45] Oct. 13, 1981

[54] TETRAHYDROISOQUINOLINE COMPOUNDS AND A PHARMACEUTICAL COMPOSITION THEREOF

[75] Inventors: Naoto Yoneda, Suita; Jyoji Kato, Yawata; Keizo Kinashi, Yao, all of Japan

[73] Assignee: Tanabe Seiyaku Co., Ltd., Osaka, Japan

[21] Appl. No.: 138,933

[22] Filed: Apr. 10, 1980

[30] Foreign Application Priority Data

Apr. 28, 1979 [JP] Japan .................................. 54/52796
Jul. 17, 1979 [JP] Japan .................................. 54/91123
Aug. 2, 1979 [JP] Japan .................................. 54/98832

[51] Int. Cl.$^3$ .................. A61K 31/47; C07D 217/16; C07D 217/24
[52] U.S. Cl. .................................. 424/258; 546/147
[58] Field of Search ........................ 546/147; 424/258

[56] References Cited

U.S. PATENT DOCUMENTS 3,691,169  9/1972  Gray ..................................... 546/147
3,691,170  9/1972  Gray ..................................... 546/147

Primary Examiner—Donald G. Daus
Assistant Examiner—J. Turnipseed
Attorney, Agent, or Firm—Bierman & Bierman

[57] ABSTRACT

A tetrahydroisoquinoline compound of the formula:

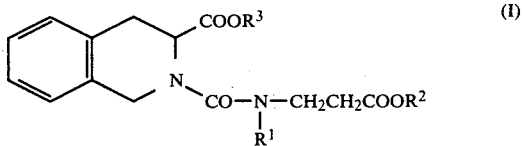

wherein $R^1$ is alkyl of one to six carbon atoms, cycloalkyl of three to six carbon atoms, allyl or propargyl, $R^2$ is hydrogen or alkyl of one to six carbon atoms, and $R^3$ is hydrogen, alkyl of one to six carbon atoms or benzyl. Methods for preparing the compound (I) are disclosed. The compound (I) and a pharmaceutically acceptable salt thereof are useful as a diagnostic or therapeutic agent for angiotensin-related hypertension.

17 Claims, No Drawings

TETRAHYDROISOQUINOLINE COMPOUNDS AND A PHARMACEUTICAL COMPOSITION THEREOF

This invention relates to a novel tetrahydroisoquinoline compound and a process for preparing same. More particularly, it relates to a compound of the general formula:

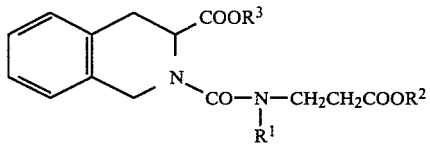

wherein $R^1$ is alkyl of one to six carbon atoms, cycloalkyl of three to six carbon atoms, allyl or propargyl, $R^2$ is hydrogen or alkyl of one to six carbon atoms, and $R^3$ is hydrogen, alkyl of one to six carbon atoms or benzyl, or a pharmaceutically acceptable salt thereof.

It is known that the enzyme renin splits a leucyl-leucine bond of angiotensinogen (a pseudoglobulin in blood plasma) to produce a decapeptide, angiotensin I. Angiotensin I is converted by angiotensin-converting enzyme (ACE) to angiotensin II which is an active pressor substance and is causative of various forms of hypertension in mammalian species. It is also known that ACE decomposes or inactivates bradykinin, the vasodepressor substance in blood plasma, thereby serving to increase blood pressure. Thus, intensive studies have been made in recent years to investigate ACE-inhibitors because such inhibitors may prevent the formation of the pressor substance angiotensin II or the decomposition of bradykinin and be used for the treatment of patients with high blood pressure. For example, M. A. Ondetti et al disclose that proline derivatives such as N-(3-mercapto-2-methylpropionyl)-L-proline intervene in the angiotensinogen→ angiotensin I→angiotensin II sequence by inhibiting angiotensin-converting enzyme and can be used in alleviating angiotensin-dependent hypertension (U.S. Pat. No. 4,046,889).

As a result of various investigations, we have now found that the novel tetrahydroisoquinoline compound (I) of the present invention shows potent inhibitory activity against angiotensin-converting enzyme (ACE) and is useful as a diagnostic or therapeutic agent for angiotensin-related hypertension. For example, when said inhibitory activity was estimated in vitro by the use of ACE isolated from pig's kidney, 3(S)-2-[N-ethyl-N-(2-carboxyethyl)carbamoyl]-1,2,3,4-tetrahydroisoquinoline-3-carboxylic acid calcium salt of the present invention showed 50% inhibition of the activity of the enzyme at a concentration of about $1.1 \times 10^{-8}$ moles/liter. Further, when the ACE-inhibitory activity was estimated in vivo by the use of rats into which angiotensin I was intravenously injected, 3(S)-2-[N-ethyl-N-(2-n-butoxycarbonylethyl)carbamoyl]-1,2,3,4-tetrahydroisoquinoline-3-carboxylic acid L-lysine salt at a dose of 0.1 mg/kg showed 80% inhibition of ACE-activity. Furthermore, when a test compound was administered orally to spontaneously hypertensive rats, 3(S)-2-[N-ethyl-N-(2-n-butoxycarbonylethyl)carbamoyl]-1,2,3,4-tetrahydroisoquinoline-3-carboxylic acid ½ calcium salt at a dose of 50 mg/kg decreased the blood pressure by 24 mm Hg. In addition, the toxicity of the compound (I) is considerably low. For example, when 3(S)-2-[N-ethyl-N-(2-n-butoxycarbonylethyl)carbamoyl]-1,2,3,4-tetrahydroisoquinoline-3-carboxylic acid ½ calcium salt was administered orally to mice at a dose of 2 g/kg, no mouse died within 7 days after said administration.

In the compound (I) of the present invention, representative examples of $R^1$ include alkyl such as methyl, ethyl, n-propyl, isopropyl, n-butyl, isobutyl, sec.-butyl and pentyl; cycloalkyl such as cyclopropyl, cyclobutyl, cyclopentyl and cyclohexyl; allyl; and propargyl. On the other hand, representative examples of $R^2$ include hydrogen; alkyl such as methyl, ethyl, n-propyl, isopropyl, n-butyl and tert.-butyl. Further, representative examples of $R^3$ include hydrogen; alkyl such as methyl, ethyl, n-propyl, isopropyl, n-butyl and tert.-butyl; and benzyl. Among those of the present invention, a preferred subgenus is the compound of the formula (I) in which $R^1$ is alkyl of one to four carbon atoms, cyclopropyl, allyl or propargyl; $R^2$ is hydrogen or alkyl of one to four carbon atoms; and $R^3$ is hydrogen. Another preferred subgenus is the compound of the formula (I) in which $R^1$ is alkyl of one to four carbon atoms, $R^2$ is hydrogen or alkyl of one to four carbon atoms, and $R^3$ is hydrogen. Further preferred subgenus is the compound of the formula (I) in which $R^1$ is alkyl of one to four carbon atoms, $R^2$ is alkyl of one to four carbon atoms and $R^3$ is hydrogen.

According to the present invention, the compound (I) can be prepared by the steps of:

(i) reacting a 1,2,3,4-tetrahydroisoquinoline-3-carboxylate compound of the formula:

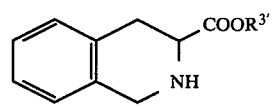

wherein $R^{3'}$ is alkyl of one to six carbon atoms or benzyl, with phosgene to give a 2-chlorocarbonyl-1,2,3,4-tetrahydroisoquinoline-3-carboxylate compound of the formula:

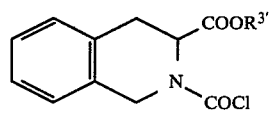

wherein $R^{3'}$ is the same as defined above, (ii) condensing the compound (III) with a N-substituted-3-aminopropionate compound of the formula:

wherein $R^1$ is the same as defined above, and $R^{2'}$ is alkyl of one to six carbon atoms, to give a 2-[N-substituted-N-(2-alkoxycarbonylethyl)carbamoyl]-1,2,3,4-tetrahydroisoquinoline-3-carboxylate compound of the formula:

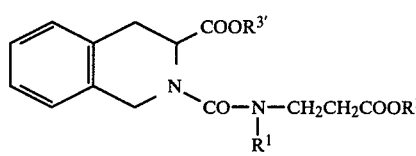

wherein $R^1$, $R^{2'}$, $R^{3'}$ are the same as defined above, and (iii-a) when $R^{2'}$ and $R^{3'}$ are alkyl of one to six carbon atoms, if required, further hydrolyzing compound (I-a) to give a 2-[N-substituted-N-(2-carboxyethyl)carbamoyl]-1,2,3,4-tetrahydroisoquinoline-3-carboxylic acid of the formula:

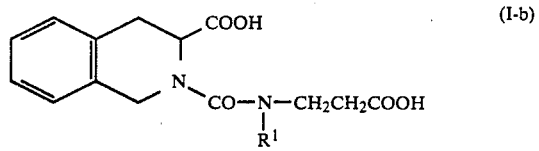

wherein $R^1$ is the same as defined above, or (iii-b) when $R^{3'}$ is benzyl, if required, further subjecting the compound (I-a) to catalytic hydrogenation to give a 2-[N-substituted-N-(2-alkoxycarbonylethyl)carbamoyl]-1,2,3,4-tetrahydroisoquinoline-3-carboxylic acid compound of the formula:

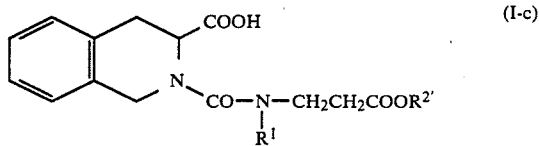

wherein $R^1$ and $R^{2'}$ are the same as defined above.

Alternatively, the compound (I-a) can be prepared by the steps of:

(i) reacting the N-substituted-3-aminopropionate compound (IV) with phosgene to give a N-chlorocarbonyl-N-substituted-3-aminopropionate compound of the formula:

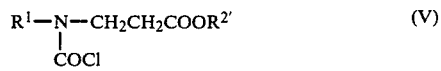

wherein $R^1$ and $R^{2'}$ are the same as defined above, and (ii) condensing the compound (V) with the 1,2,3,4-tetrahydroisoquinoline-3-carboxylate compound (II).

The starting compound (II) of the invention may be obtained by condensing phenylalanine with formaldehyde (Journal of The American Chemical Society 70, 180(1948), and then esterifying the resultant 1,2,3,4-tetrahydroisoquinoline-3-carboxylic acid. On the other hand, the starting compound (IV) may be obtained by condensing an acrylate of the formula: $CH_2=CHCOOR^{2'}$ (wherein $R^{2'}$ is the same as defined above) with a primary amine of the formula: $R^1—NH_2$ (wherein $R^1$ is the same as defined above) (R. B. Wagner et al: Synthertic Organic Chemistry, 673(1961)).

The reaction of the compound (II) or (IV) with phosgene can be accomplished in the presence or absence of an acid acceptor in a solvent. Preferred examples of the acid acceptor include triethylamine, tripropylamine, N-methylmorpholine, pyridine and the like. Methylene chloride, chloroform, tetrahydrofuran and dioxane are suitable as the solvent. It is preferred to carry out the reaction at a temperature between −40° and 0° C.

The condensation reaction of the compound (III) with the compound (IV) or the condensation reaction of the compound (V) with the compound (II) can be conducted in the presence of an acid acceptor in a solvent. Preferred examples of the acid acceptor include triethylamine, tripropylamine, N-methylmorpholine, pyridine and the like. Methylene chloride, chloroform, tetrahydrofuran, dioxane and dimethylformamide are suitable as the solvent. It is preferred to carry out the reaction at a temperature between 0° and 80° C., especially 35° and 40° C.

The hydrolysis of the compound (I-a) in which $R^{2'}$ and $R^{3'}$ are alkyl of one to six carbon atoms can be easily accomplished. For example, when the compound (I-a) in which $R^{2'}$ and $R^{3'}$ are alkyl other than t-butyl is employed, the hydrolysis of said compound can be carried out by treating it with an alkali in a solvent. Suitable examples of the alkali include an alkali metal hydroxide (e.g., sodium hydroxide, potassium hydroxide) and an alkali metal carbonate (e.g., sodium carbonate, potassium carbonate). A mixture of an alkanol (e.g., methanol, ethanol, propanol) and water is suitable as the solvent. It is preferred to carry out the reaction at a temperature between 0° and 100° C., especially 20° and 40° C. On the other hand, when the compound (I-a) in which $R^{2'}$ and $R^{3'}$ are t-butyl is employed, the hydrolysis of said compound can be carried out by treating it with an acid in a solvent. Suitable examples of the acid include trifluoroacetic acid, hydrochloric acid, sulfuric acid and the like. An alkanol (e.g., methanol, ethanol) is suitable as the solvent. When trifluoroacetic acid is employed as the acid, however, it is not always necessary to use the solvent because said acid serves as the solvent. It is preferred to carry out the reaction at a temperature between 0° and 80° C., especially 20° and 40° C. Futher, when the compound (I-a) in which one of $R^{2'}$ and $R^{3'}$ is t-butyl and the other is alkyl other than t-butyl is employed, the hydrolysis of said compound can be conducted either by treating it with an alkali followed by treatment with an acid or by treating it with an acid followed by treatment with an alkali. The alkali and acid hydrolysises can be carried out in the same manner as described above.

The catalytic hydrogenation of the compound (I-a) in which $R^{3'}$ is benzyl can be accomplished in the presence of a catalyst in a solvent. Preferred examples of the catalyst include palladium-black, palladium-carbon, platinum dioxide and the like. An alkanol (e.g., methanol, ethanol, propanol) is suitable as the solvent. It is preferred to carry out the reaction at a temperature between 20° and 60° C., especially 20° and 40° C. It is also preferred to carry it out under one to 5 atmospheric pressures.

The compound (I) of the present invention can be used for pharmaceutical use either as the free acid or a salt thereof. Pharmaceutically acceptable salts of the compound (I) include, for example, inorganic salts such as sodium, potassium, calcium and magnesium salts, organic salts such as lysine and arginine salts, and the like. A daily dose of the compound (I) or a salt thereof may be about 30 mg to about 3 g, especially 50 mg to one g, per body of patients. Further, the compound (I) or a salt thereof may be used in the form of a pharmaceutical preparation containing the same compound in conjunction or admixture with a pharmaceutical excipient suitable for oral or parenteral administration. Suitable excipients include, for example, starch, lactose, glucose, potassium phosphate, corn starch, arabic gum, stearic acid and other known medicinal excipients. The pharmaceutical preparations may be in solid form such as tablets, pills or capsules; or in liquid form such as solutions, suspensions or emulsions. They may be sterilized and/or may further contain auxiliaries such as stabilizing, wetting or emulsifying agents. While the compound (I) involves two optical isomers due to the assymetric carbon atom at the 3th-position in the isoquinoline ring, either one of said optical isommers or a mixture thereof may be used for medicinal purposes.

EXPERIMENT 1

ACE-inhibitory activity in vitro:

50 μl of a solution containing 0.01 mole/liter of hippuryl-histidyl-leucine (substrate) and 0–100 μl of a test compound solution were added to 300 μl of a 0.2M trishydrochloric acid buffer solution containing 0.2 mole/liter of sodium chloride. The total volume of said mixture was adjusted to 450 μl with water. Then, 50 μl of angiotensin -converting enzyme (ACE) isolated from pig's renal cortex were added to the mixture, and the mixture was allowed to stand at 37° C. for 20 minutes. The amount of histidyl-leucine produced from the substrate by the action of ACE was assayed microbiologically by the use of Leuconostoc mesenteroides P-60, and the ACE-inhibitory activity of the test compound was estimated therefrom. The results are shown in the following Table 1.

TABLE 1

| Test compounds | ACE-inhibitory activity in vitro $I_{50}$ (mol/liter)* |
|---|---|
| 3(S)-2-[N-methyl-N-(2-carboxyethyl)-carbamoyl]-1,2,3,4-tetrahydro-isoquinoline-3-carboxylic acid di-dicyclohexylamine salt | $6.1 \times 10^{-7}$ |
| 3(S)-2-[N-ethyl-N-(2-carboxyethyl)-carbamoyl]-1,2,3,4-tetrahydro-isoquinoline-3-carboxylic acid calcium salt | $1.1 \times 10^{-8}$ |
| 3(S)-2-[N-ethyl-N-2-carboxyethyl)-carbamoyl]-1,2,3,4-tetrahydro-isoquinoline-3-carboxylic acid di-sodium salt | $2.1 \times 10^{-8}$ |
| 3(S)-2-[N-n-propyl-N-(2-carboxyethyl)-carbamoyl]-1,2,3,4-tetrahydro-isoquinoline-3-carboxylic acid di-dicyclohexylamine salt | $5.5 \times 10^{-7}$ |
| 3(S)-2-[N-isopropyl-N-(2-carboxyethyl)-carbamonyl]-1,2,3,4-tetrahydro-isoquinoline-3-carboxylic acid di-L-lysine salt | $2.9 \times 10^{-8}$ |
| 3(S)-2-[N-cyclopropyl-N-(2-carboxy-ethyl)carbamoyl]-1,2,3,4-tetrahydro-isoquinoline-3-carboxylic acid di-dicyclohexylamine salt | $1.4 \times 10^{-7}$ |
| 3(S)-2-[N-allyl-N-(2-carboxyethyl)-carbamoyl]-1,2,3,4-tetrahydro-isoquinoline-3-carboxylic acid di-L-lysine salt | $1.4 \times 10^{-7}$ |
| 3(S)-2-[N-propargyl-N-(2-carboxyethyl)-carbamoyl]-1,2,3,4-tetrahydro-isoquinoline-3-carboxylic acid di-L-lysine salt | $3.5 \times 10^{-8}$ |

Note:
*$I_{50}$ = a dose required to induce 50% inhibition of the ACE activity

EXPERIMENT 2

ACE-inhibitory activity in vivo:

Normotensive rats weighing 300–400 g were anesthetized with urethane (1.5 g/kg, s.c.), and angiotensin I (300 ng/kg) was injected into the femoral vein of the rats. The pressor response to angiotensin I was measured with a pressure transducer connected to the carotid artery. Then, a test compound was injected intravenously thereto at a dose of 0.1 mg/kg, and angiotensin I (300 ng/kg) was further injected intravenously at intervals. The ACE-inhibitory activity of the test compound was estimated from the pressur responses to angiotensin I which were obtained before and after intravenous injection of the test compound. The results are shown in the following Table 2.

TABLE 2

| Test compounds | ACE-inhibitory activity in vivo (%)* | Duration of activity (minutes) |
|---|---|---|
| 3(S)-2-[N-isopropyl-N-(2-carboxyethyl)carbamoyl]-1,2,3,4-tetrahydroisoquinoline-3-carboxylic acid di-dicyclohexylamine salt | >60 | >60 |
| 3(S)-2-[N-methyl-N-(2-ethoxycarbonylethyl)carbamoyl]-1,2,3,4-tetrahydro-isoquinoline-3-carboxylic acid L-lysine salt | 40–60 | >60 |
| 3(S)-2-[N-ethyl-N-(2-ethoxycarbonylethyl)carbamoyl]-1,2,3,4-tetrahydro-isoquinoline-3-carboxylic acid L-lysine salt | >60 | >60 |
| 3(S)-2-[N-ethyl-N-(2-n-butoxy-carbonylethyl)carbamoyl]-1,2,3,4-tetrahydroisoquinoline-3-carboxylic acid L-lysine salt | >60 | >60 |
| 3(S)-2-[N-isopropyl-N-(2-methoxycarbonylethyl)carbamoyl]-1,2,3,4-tetrahydroisoquinoline-3-carboxylic acid L-lysine salt | 40 – 60 | 30 – 60 |
| 3(S)-2-[N-isopropyl-N-(2-methoxycarbonylethyl)carbamoyl]-1,2,3,4-tetrahydroisoquinoline-3-carboxylic acid sodium salt | 40 – 60 | >60 |
| 3(S)-2-[N-isopropyl-N-(2-ethoxycarbonylethyl)carbamoyl]-1,2,3,4-tetrahydroisoquinoline-3-carboxylic acid L-lysine salt | >60 | >60 |
| 3(S)-2-[N-isopropyl-N-(2-n-butoxycarbonylethyl)carbamoyl]-1,2,3,4-tetrahydroisoquinoline-3-carboxylic acid L-lysine salt | >60 | >60 |

Note:
*percentage inhibition of ACE activity in vivo

EXPERIMENT 3

Hypotensive activity in SHR:

A test compound (dose: 50 mg/kg) suspended in an aqueous carboxymethylcellulose solution was administered orally to spontaneously hypertensive rats (SHR) fasted overnight. The systolic blood pressure of the rats was measured by the tail plethysmographic technique (The Journal of Laboratory and Clinical Medicine 78(1971), page 957). The hypotensive activity of the test compound was estimated from the decreased level of blood pressure. The results are shown in the following Table 3.

TABLE 3

| Test compounds | Hypotensive activity in SHR | |
|---|---|---|
| | Decrease in blood pressure ($-\Delta$ mm Hg) | Duration of action (hours) |
| 3(S)-2-[N-ethyl-N-(2-ethoxycarbonylethyl)carbamoyl]-1,2,3,4-tetrahydroisoquinoline-3-carboxylic acid ½ calcium salt | 26 | >6 |
| 3(S)-2-[N-ethyl-N-(2-n-ethoxycarbonylethyl)carbamoyl]-1,2,3,4-tetrahydroisoquinoline-3-carboxyleic acid L-lysine salt | 25 | >6 |
| 3(S)-2-[N-ethyl-N-(2-n-butoxycarbonylethyl)carbamoyl]-1,2,3,4-tetrahydroisoquinoline-3-carboxylic acid ½ calcium salt | 24 | >6 |
| 3(S)-2-[N-isopropyl-N-(2-methoxy- | | |

TABLE 3-continued

| Test compounds | Hypotensive activity in SHR | |
|---|---|---|
| | Decrease in blood pressure ($-\Delta$ mm Hg) | Duration of action (hours) |
| carbonylethyl)carbamoyl]-1,2,3,4-tetrahydroisoquinoline-3-carboxylic acid L-lysine salt | 36 | >6 |

EXAMPLE 1

A solution of 3.0 g of phosgene in 20 ml of methylene chloride is cooled to −30° to −20° C., and a solution of 3.8 g of methyl 3(S)-1,2,3,4-tetrahydroisoquinoline-3-carboxylate and 3.0 g of triethylamine in 20 ml of methylene chloride is dropwise added thereto under stirring. After the mixture is stirred at the same temperature for 30 minutes, said mixture is condensed under reduced pressure to dryness. The residue (i.e., methyl 3(S)-2-chlorocarbonyl-1,2,3,4-tetrahydroisoquinoline-3-carboxylate) is dissolved in 20 ml of methylene chloride, and a solution of 2.34 g of methyl 3-methylaminopropionate and 2.4 g of triethylamine in 10 ml of methylene chloride is dropwise added thereto at room temperature under stirring. The mixture is stirred at the same temperature for 15 hours. After the reaction, the reaction mixture is condensed under reduced pressure to dryness. The residue thus obtained is dissolved in ethyl acetate, and the solution is washed with dilute hydrochloric acid, an aqueous sodium bicarbonate solution and water, successively. Then, the solution is dried and evaporated to remove solvent. The residue thus obtained is purified by silica gel chromatography (Solvent: chloroform-ethyl acetate (6:1)), whereby 3.0 g of methyl 3(S)-2-[N-methyl-N-(2-methoxycarbonylethyl)-carbamoyl]-1,2,3,4-tetrahydroisoquinoline-3-carboxylate are obtained as a colorless viscous oil. Yield: 44.8%

IR $\nu_{max}^{film}$(cm$^{-1}$): 1740, 1640

NMR (CDCl$_3$)δ: 7.05–7.2(m, 4H, aromatic H), 4.76(t, 1H, >C$\underline{H}$—N), 4.50(s, 2H, Ar-C$\underline{H_2}$—N), 3.63(s, 6H, O—C$\underline{H_3}$×2), 3.45(t, 2H, —N—C$\underline{H_2}$), 3.17(d, 2H, Ar—C$\underline{H_2}$—C), 2.93(s, 3H, N—C$\underline{H_3}$), 2.59(t, 2H, —C$\underline{H_2}$—CO)

Mass M/e: 334 (M+)

EXAMPLE 2

2.0 g of methyl 3(S)-2-[N-metyl-N-(2-methoxycarbonylethyl)carbamoyl]-1,2,3,4-tetrahydroisoquinoline-3-carboxylate are dissolved in 6 ml of methanol, and 6 ml of water and 1.2 g of potassium hydroxide are added thereto. After the mixture is stirred at room temperature for 2 hours, said mixture is evaporated under reduced pressure to remove solvent. The residue is acidified with dilute hydrochloric acid, and then extracted with chloroform. The extract is washed with water and then dried. Then, 2.2 g of dicyclohexylamine are added to the extract, and the mixture is condensed to dryness. The residue is crystallized with ether, whereby 2.0 g of 3(S)-2-[N-methyl-N-(2-carboxyethyl)carbamoyl]-1,2,3,4-tetrahydroisoquinoline-3-carboxylic acid 2 dicyclohexylamine salt are obtained as colorless crystalline powder. Yield: 50%

M.p. 67°–68° C. (decomp.)

$[\alpha]_{365}^{20}$ −10.4° (C=1, methanol)

EXAMPLE 3

3.8 g of methyl 3(S)-1,2,3,4-tetrahydroisoquinoline-3-carboxylate, 2.6 g of methyl 3-ethylaminopropionate, 3 g of phosgene, 5.4 g of triethylamine and 70 ml of methylene chloride are treated in the same manner as described in Example 1. The crude product thus obtained is purified by silica gel chromatography (Solvent: toluene-ethyl acetate(3:1)), whereby 5.0 g of methyl 3(S)-2-[N-ethyl-N-(2-methoxycarbonylethyl)carbamoyl]-1,2,3,4-tetrahydroisoquinoline-3-carboxylate are obtained as colorless crystals. Yield: 71.8%

M.p. 53°–55° C. (colorelss prisms) (recrystallized from a mixture of ethyl acetate and n-hexane)

IR$\nu_{max}^{Nujol}$(cm$^{-1}$): 1738, 1725, 1635

NMR (CDCl$_3$)δ: 7.0–7.2(m, 4H, aromatic H), 4.80(t, 1H, >C$\underline{H}$—N), 4.52(s, 2H, Ar—C$\underline{H_2}$—N), 3.66(s, 3H, O—C$\underline{H_3}$), 3.64(s, 3H, O—C$\underline{H_3}$), 3.19(d, 2H, Ar—C$\underline{H_2}$—CH), 3.1–3.5(m, 4H, N—C$\underline{H_2}$—CH$_3$ and N—CH$_2$—C$\underline{H_2}$—), 2.57(t, 2H, C$\underline{H_2}$—CO), 1.20(t, 3H, N—CH$_2$—C$\underline{H_3}$)

Mass m/e: 348 (M+)

$[\alpha]_D^{20}$ −1.2° (C=1, methanol)

EXAMPLE 4

A solution of 3.0 g of phosgene in 20 ml of methylene chloride is cooled to −30° to −20° C., and a solution of 2.6 g of methyl 3-ethylaminopropionate and 3.0 g of triethylamine in 20 ml of methylene chloride is dropwise added thereto under stirring. The mixture is stirred at the same temperature for about 30 minutes, and said mixture is condensed under reduced pressure to dryness. 20 ml of methylene chloride are added to the residue (i.e., methyl N-chlorocarbonyl-3-ethylaminopropionate), and a solution of 3.8 g of methyl 3(S)-1,2,3,4-tetrahydroisoquinoline-3-carboxylate and 2.4 g of triethylamine in 10 ml of methylene chloride is dropwise added thereto at room temperature under stirring. After the reaction, the reaction mixture is treated in the same manner as described in Example 3. 4.8 g of methyl 3(S)-2-[N-ethyl-N-(2-methoxycarbonylethyl)carbamoyl]-1,2,3,4-tetrahydroisoquinoline-3-carboxylate are thereby obtained as colorless crystals. Yield: 68.9%

The physico-chemical properties of this product are identical with those of the product obtained in Example 3.

EXAMPLE 5

2.1 g of methyl 3(S)-2-[N-ethyl-N-(2-methoxycarbonylethyl)carbamoyl]-1,2,3,4-tetrahydroisoquinoline-3-carboxylate are dissolved in 6 ml of methanol, and 1.2 g of potassium hydroxide and 6 ml of water are added thereto. After the mixture is stirred at room temperature for 2 hours, said mixture is evaporated under reduced pressure to remove solvent. The residue is acidified with dilute hydrochloric acid, and then extracted with chloroform. The extract is washed with water, dried and then evaporated to remove solvent. The residue thus obtained is crystallized with n-hexane, whereby 1.5 g of 3(S)-2-[N-ethyl-N-(2-carboxyethyl)carbamoyl]-1,2,3,4-tetrahydroisoquinoline-3-carboxylic acid are obtained as colorless powder. Yield: 78.1%

M.p. 123°–125° C. (decomp.)

IR$\nu_{max}^{nujol}$(cm$^{-1}$): 1720, 1630

$[\alpha]_D^{20}$ −11.3° (C=1, methanol)

Di-dicyclohexylamine salt:
 colorless crystalline powder
 M.p. 135°–137° C. (decomp.)

$[\alpha]_{365}^{20} -19.7°$ (C=1, methanol)

Di-potassium salt:

A solution of 0.57 g of potassium carbonate in 30 ml of water is added to 1.31 g of 3(S)-2-[N-ethyl-N-(2-carboxyethyl)carbamoyl]-1,2,3,4-tetrahydroisoquinoline-3-carboxylic acid, and the mixture is vigorously stirred at room temperature for about one hour. The reaction mixture is lyophilized, whereby 1.62 g of 3(S)-2-[N-ethyl-N-(2-carboxyethyl)carbamoyl]-1,2,3,4-tetrahydroisoquinoline-3-carboxylic acid di-potassium salt are obtained as colorless powder.

Di-sodium salt:
 colorless powder

Di-L-lysine salt:
 colorless crystalline powder

Calcium salt:
 colorless powder

EXAMPLE 6

A solution of 3.0 g of phosgene in 40 ml of methylene chloride is cooled to $-30°$ to $-20°$ C., and a solution of 4.7 g of t-butyl 3(S)-1,2,3,4-tetrahydroisoquinoline-3-carboxylate and 3.0 g of triethylamine in 20 ml of methylene chloride is dropwise added thereto. After the mixture is stirred at the same temperature for 30 minutes, said mixture is condensed under reduced pressure. 20 ml of methylene chloride are added to the residue (i.e., t-butyl 3(S)-2-chlorocarbonyl-1,2,3,4-tetrahydroisoquinoline-3-carboxylate), and a solution of 3.5 g of t-butyl 3-ethylaminopropionate and 2.4 g of triethylamine in 10 ml of methylene chloride is dropwise added thereto. Then, the mixture is stirred at about 50° C. for 15 hours. The reaction mixture is condensed under reduced pressure, and the residue is dissolved in ethyl acetate. The solution is washed with an aqueous 10% citric acid solution, an aqueous sodium bicarbonate solution and water, successively. Said solution is dried and then evaporated to remove solvent. The residue thus obtained is purified by silica gel chromatography (Solvent: toluene-ethyl acetate (6:1)). 3.9 g of t-butyl 3(S)-2-[N-ethyl-N-(2-t-butoxycarbonylethyl)carbamoyl]-1,2,3,4-tetrahydroisoquinoline-3-carboxylate are thereby obtained as a colorless viscous oil. Yield: 44.8%

IR$\nu_{max}^{film}$(cm$^{-1}$): 1735, 1640

NMR (CDCl$_3$)$\delta$: 7.1–7.2(m, 4H, aromatic H), 4.74(t, 1H, >C$\underline{H}$—N), 4.53(s, 2H, Ar—C$\underline{H}_2$—N), 3.1–3.6(m, 4H, N—C$\underline{H}_2$×2), 3.16(d, 2H, Ar—C$\underline{H}_2$—CH), 2.57(t, 2H, C$\underline{H}_2$—CO), 1.42(s, 9H, C$\underline{H}_3$×3), 1.32(s, 9H, C$\underline{H}_3$×3), 1.2(t, 3H, —CH$_2$—C$\underline{H}_3$)

Mass m/e: 432 (M+)

EXAMPLE 7

20 ml of trifluoroacetic acid are added to 1.7 g of t-butyl 3(S)-2-[N-ethyl-N-(2-t-butoxycarbonylethyl)carbamoyl]-1,2,3,4-tetrahydroisoquinoline-3-carboxylate, and the mixture is stirred at room temperature for 30 minutes. Then, the reaction mixture is condensed under reduced pressure to dryness, and the residue is crystallized with n-hexane. 1.0 g of 3(S)-2-[N-ethyl-N-(2-carboxyethyl)carbamoyl]-1,2,3,4-tetrahydroisoquinoline-3-carboxylic acid is thereby obtained as colorless crystals.

The physico-chemical properties of this product are identical with those of the product obtained in Example 5.

EXAMPLE 8

3.8 g of methyl 3(S)-1,2,3,4-tetrahydroisoquinoline-3-carboxylate, 2.9 g of methyl 3-n-propylaminopropionate, 3.0 g of phosgene and 5.4 g of triethylamine are treated in the same manner as described in Example 1. 5.2 g of methyl 3(S)-2-[N-n-propyl-N-(2-methoxycarbonylethyl)carbamoyl]-1,2,3,4-tetrahydroisoquinoline-3-carboxylate are thereby obtained as a colorless viscous oil. Yield: 71.7%

IR$\nu_{max}^{film}$(cm$^{-1}$): 1740, 1640

NMR (CDCl$_3$)$\delta$: 7.1–7.2(m, 4H, aromatic H), 4.80(t, 1H, >C$\underline{H}$—N), 4.53(s, 2H, Ar—C$\underline{H}_2$—N), 3.68(s, 3H, O—C$\underline{H}_3$), 3.65(s, 3H, O—C$\underline{H}_3$), 3.2–3.6(m, 4H, N—C$\underline{H}_2$×2), 3.14(d, 2H, Ar—C$\underline{H}_2$—CH<), 2.59(t, 2H, C$\underline{H}_2$—CO), 1.3–2.0(m, 2H, C$\underline{H}_2$—CH$_2$—CH$_3$), 0.9(t, 3$\overline{H}$, C$\underline{H}_3$)

Mass m/e: 362 (M+)

EXAMPLE 9

3.6 g of methyl 3(S)-2-[N-n-propyl-N-(2-methoxylcarbonylethyl)carbamoyl]-1,2,3,4-tetrahydroisoquinoline-3-carboxylate are treated in the same manner as described in Example 2. 4.0 g of 3(S)-2-[N-n-propyl-N-(2-carboxyethyl)carbamoyl]-1,2,3,4-tetrahydroisoquinoline-3-carboxylic acid 2 dicyclohexylamine salt are therebt obtained as colorless crystalline powder. Yield: 57.4%

M.p. 127°–128° C. (decomp.)

EXAMPLE 10

3.8 g of methyl 3(S)-1,2,3,4-tetrahydroisoquinoline-3-carboxylic acid, 2.9 g of methyl 3-isopropylaminopropionate, 3.0 g of phosgene and 5.4 g of triethylamine are treated in the same manner as described in Example 1. 4.4 g of methyl 3(S)-2-[N-isopropyl-N-(2-methoxycarbonylethyl)carbamoyl]-1,2,3,4-tetrahydroisoquinoline-3-carboxylate are thereby obtained as colorless crystals. Yiled: 61.1%

M.p. 78°–79° C.(colorless prisms) (recrystallized from a mixture of ethyl acetate and n-hexane)

IR$\nu_{max}^{nujol}$(cm$^{-1}$): 1735, 1640

NMR (CDCl$_3$) $\delta$: 7.1–7.2(m, 4H, aromatic H), 4.79(t, 1H, >C$\underline{H}$—N), 4.51(s, 2H, Ar—C$\underline{H}_2$—N), 3.5–4.1(m, 1H, C$\underline{H}$(CH$_3$)$_2$), 3.66(s, 3H, O—C$\underline{H}_3$), 3.59(s, 3H, O—C$\underline{H}_3$), 3.27(t, 2H, N—C$\underline{H}_2$), 3.19(d, 2H, Ar—C$\underline{H}_2$—CH), 2.49(t, 2H, C$\underline{H}_2$—CO), 1.26(d, 3H, >CH—C$\underline{H}_3$), 1.16(d, 3H, >CH—C$\underline{H}_3$)

Mass m/e: 362 (M+)

$[\alpha]_D^{20} -0.35°$ (C=1, methanol)

EXAMPLE 11

3.4 g of methyl 3(S)-2-[N-isopropyl-N-(2-methoxycarbonylethyl)carbamonyl]-1,2,3,4-tetrahydroisoquinoline-3-carboxylate are treated in the same manner as described in Example 5. 2.7 g of 3(S)-2-[N-isopropyl-N-(2-carboxyethyl)carbamoyl]-1,2,3,4-tetrahydroisoquinoline-3-carboxylic acid are thereby obtained as colorless powder. Yield: 86.0%

M.p. 72°–73° C. (decomp.)

IR$\nu_{max}^{KBr}$(cm$^{-1}$): 1720, 1630

$[\alpha]_D^{20} -9.7°$ (C=1, methanol)

Di-L-lysine salt:
 colorless powder

Di-dicyclohexylamine salt:
 colorless crystalline powder
 M.p. 92°–94° C. (decomp.)
 $[\alpha]_{365}^{20} -14.6°$ (C=1, methanol)

EXAMPLE 12

3.8 g of methyl 3(S)-1,2,3,4-tetrahydroisoquinoline-3-carboxylate, 2.9 g of methyl 3-cyclopropylaminopropionate, 3.0 g of phosgene and 5.4 g of triethylamine are treated in the same manner as described in Example 1. 5.0 g of methyl 3(S)-2-[N-cyclopropyl-N-(2-methoxycarbonylethyl)carbamoyl]-1,2,3,4-tetrahydroisoquinoline-3-carboxylate are thereby obtained as a colorless viscous oil. Yield: 69.3%

IR$\nu_{max}^{film}$(cm$^{-1}$): 1740, 1630

NMR (CDCl$_3$)δ: 7.1–7.2(m, 4H, aromatic H), 4.93(t, 1H, >C$\underline{H}$—N), 4.67(s, 2H, Ar—C$\underline{H}_2$—N),

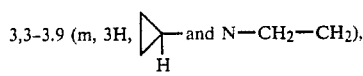

3.67(s, 3H, O—C$\underline{H}_3$), 3.63(s, 3H, O—C$\underline{H}_3$), 3.21(d, 2H, Ar—C$\underline{H}_2$—CH<), 2.62(t, 2H, —C$\underline{H}_2$—CO),

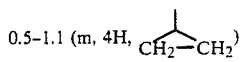

Mass m/e: 360 (M$^+$)

EXAMPLE 13

2.4 g of methyl 3(S)-2-[N-cyclopropyl-N-(2-methoxycarbonylethyl)carbamoyl]-1,2,3,4-tetrahydroisoquinoline-3-carboxylate are treated in the same manner as described in Example 2. 3.1 g of 3(S)-2-[N-cyclopropyl-N-(2-carboxyethyl)-carbamoyl]-1,2,3,4-tetrahydroisoquinoline-3-carboxylic acid di-dicyclohexylamine salt are thereby obtained as colorless crystalline powder. Yield: 67%

M.p. 92°–93° C. (decomp.)

$[\alpha]_{365}^{20}$ −16.5° (C=1, methanol)

EXAMPLE 14

2.9 g of methyl 3(S)-1,2,3,4-tetrahydroisoquinoline-3-carboxylic acid, 2.9 g of methyl 3-allylaminopropionate, 3.0 g of phosgene and 5.4 g of triethylamine are treated in the same manner as described in Example 1. 5.0 g of methyl 3(S)-2-[N-ally-N-(2-methoxycarbonylethyl)carbamoyl]-1,2,3,4-tetrahydroisoquinoline-3-carboxylate are thereby obtained as a colorless viscous oil.

Yield: 69.9%

IR$\nu_{max}^{film}$(cm$^{-1}$): 1740, 1640

NMR (CDCl$_3$)δ: 7.0–7.2(m, 4H, aromatic H), 5.5–6.0(m, 1H, CH$_2$=C$\underline{H}$—), 5.0–5.45(m, 2H, C$\underline{H}_2$=CH—), 4.80(t, 1H, >C$\underline{H}$—N), 4.51(s, 2H, Ar—C$\underline{H}_2$—N), 3.7–3.95(m, 2H, —N—C$\underline{H}_2$—CH=), 3.66(s, 3H, O—C$\underline{H}_3$), 3.63(s, 3H, O—C$\underline{H}_3$), 3.25–3.6(m, 2H, N—C$\underline{H}_2$—CH$_3$), 3.19(d, 2H, Ar—C$\underline{H}_2$—CH), 2.59(t, 2H, C$\underline{H}_2$—CO)

Mass m/e: 360 (M$^+$)

EXAMPLE 15

2.4 g of methyl 3(S)-2-[N-allyl-N-(2-methoxycarbonylethyl)carbamoyl]-1,2,3,4-tetrahydroisoquinoline-3-carboxylate are treated in the same manner as described in Example 5. 1.4 g of 3(S)-2-[N-allyl-N-(2-carboxyethyl)carbamoyl]-1,2,3,4-tetrahydroisoquinoline-3-carboxylic acid are thereby obtained as colorless crystalline powder.

Yield: 63.3%

M.p. 76°–78° C. (decomp.)
IR$\nu_{max}^{KBr}$(cm$^{-1}$):1720, 1630

EXAMPLE 16

3.8 g of methyl 3(S)-1,2,3,4-tetrahydroisoquinoline-3-carboxylate, 2.82 g of methyl propargylaminopropionate, 3.0 g of phosgene, 5.4 g of triethylamine and 70 ml of methylene chloride are treated in the same manner as described in Example 1. The crude product is purified by silica gel chromatography(Solvent: toluene-ethyl acetate(4:1)). 3.1 g of methyl (3)-2-[N- propargyl-N-(2-methoxycarbonylethyl)-carbamoyl]-1,2,3,4-tetrahydroisoquinoline-3-carboxylate are thereby obtained as a colorless oil.

Yield: 43.2%

IR$\nu_{max}^{film}$(cm$^{-1}$): 3280, 1738, 1645

NMR (CDCl$_3$)δ: 7.0–7.3(m, 4H, aromatic H), 4.87(t, 1H, >C$\underline{H}$—N), 4.62(s, 2H, Ar—C$\underline{H}_2$—N), 4.01(d, 2H, C$\underline{H}_2$—C≡C), 3.69(s, 6H, O—C$\underline{H}_3$×2), 3.62(t, 2H, —N—C$\underline{H}_2$—CH$_2$), 3.23(d, 2H, Ar—C$\underline{H}_2$—CH), 2.67(t, 2H, —C$\underline{H}_2$—CO), 2.33(t, 1H, —C≡C$\underline{H}$)

Mass m/e: 358 (M$^+$)

EXAMPLE 17

2.77 g of methyl 3(S)-2-[N-propargyl-N-(2-methoxycarbonylethyl)carbamoyl]-1,2,3,4-tetrahydroisoquinoline-3-carboxylate are dissolved in 8 ml of methanol, and 1.53 g of potassium hydroxide and 8 ml of water are added thereto. After the mixture is stirred at room temperature for 2 hours, said mixture is evaporated under reduced pressure to remove solvent. The residue is acidified with dilute hydrochloric acid, and then extracted with chloroform. The extract is washed with water, dried and then evaporated to remove solvent. 2.16 g of 3(S)-2-[N-propargyl-N-(2-carboxyethyl)carbamoyl]-1,2,3,4-tetrahydroisoquinoline-3-carboxylic acid are thereby obtained as a coloreless oil.

Yield: 85.0%.

A solution of 1.86 g L-lysine in 30 ml of water is added to 2.1 g of the oil obtained above, and the mixture is vigorously stirred at room temperature for about one hours. The reaction mixture is condensed to dryness, and ether is added to the residue. The precipitates are collected by filtration, whereby 3.5 g of 3(S)-2-[N-propargyl-N -(2-carboxyethyl)carbamoyl]-1,2,3,4-tetrahydroisoquinoline-3-carboxylic acid di-L-lysine salt are obtained as colorless powder.

M.p. 199°–200° C. (decomp.)

EXAMPLE 18

(1) A mixture pf 10.7 g of 3(S)-1,2,3,4-tetrahydroisoquinoline-3-carboxylic acid hydrochloride, 27 g of benzylalcohol, 11.5 of p-toluenesulfonic acid monohydrate and 150 ml of toluene is refluxed for 6 hours while removing the resultant water. After cooling, the reaction mixture is evaporated to remove solvent. Ether is added to the residue, and the crystalline precipitates are collected by filtration. 20 g of benzyl 3(S)-1,2,3,4-tetrahydroisoquinoline-3-carboxylate p-toluenesulfoic acid salt are thereby obtained.

Yield: 91%

M.p. 146°–148° C. (colorless needles) (recrystallized from aqueous methanol)

IR$\nu_{max}^{nujol}$(cm$^{-1}$): 1740

$[\alpha]_D^{27}$ −55.3° (C=1, methanol)

The product obtained above is dissolved in an aqueous sodium bicarbonate solution, and then extracted with chloroform. The extract is dried and then evaporated to remove solvent. Benzyl 3(S)-1,2,3,4-tetrahydroisoquinoline-3-carboxylate is obtained as a colorless viscous oil.

(2) 5.3 g of benzyl 3(S)-1,2,3,4-tetrahydroisoquinoline-3-carboxylate and 3.0 g of triethylamine are dissolved in 20 ml of methylene chloride. To a soulution of 3.0 g of phosgene in 20 ml of methylene chloride are dropwise added the carboxylate solution at $-30°$ to $-20°$ C. under stirring. The mixture is further stirred at the same temperature for 30 minutes. The reaction mixture is condensed under reduced pressure to dryness. The residue (i.e., benzyl 3(S)-2-chlorocarbonyl-1,2,3,4-tetrahydroisoquinoline-3-carboxylate) is dissolved in 20 ml of methylene chloride. A solution of 2.62 g of ethyl 3-methylaminopropionate (B.p. 83°–84° C./34 mm Hg) and 2.4 g of triethylamine in 10 ml of methylene chloride is added dropwise to the carboxylate solution at room temperature under stirring. The mixture is further stirred at 30°–35° C. for about 15 hours. After the reaction, the reaction mixture is condensed under reduced pressure to dryness, and the residue is dissolved in ethyl acetate. The solution is washed with dil. hydrochloric acid, and aqueous sodium bicarbonate solution and water, successively. Then, the solution is dried and then evaporated to remove solvent. The oily residue is purified by silica gel chromatography (Solvent: toluene-ethyl acetate (5:1)). 6.9 g of benzyl 3(S)-2-[N-methyl-N-(2-ethoxycarbonylethyl)carbamoyl]-1,2,3,4-tetrahydroisoquinoline-3-carboxylate are thereby obtained as a colorless oil.

Yield: 81.2%

IR$\nu_{max}^{film}$(cm$^{-1}$): 1735, 1640

NMR (CDCl$_3$)$\delta$: 6.9–7.4(m, 9H, aromatic H), 5.09 (s, 2H, —C$\underline{H}_2$—Ph), 4.85(t, 1H, >C$\underline{H}$—N), 4.51(s, 2H, Ar—C$\underline{H}_2$—N), 4.08(q, 2H, O—C$\underline{H}_2$CH$_3$), 3.55(t, 2H, N—C$\underline{H}_2$—CH$_2$—), 3.22(d, 2H, Ar—C$\underline{H}_2$—C), 2.91(S, 3H, N—CH$_3$), 2.56 (t, 2H, —C$\underline{H}_2$—COO—), 1.21(t, 3H, O—CH$_2$C$\underline{H}_3$)

Mass m/e: 424 (M$^+$)

$[\alpha]_D^{27}$ $-1.3°$ (C=2, methanol)

EXAMPLE 19

A mixture of 5.9 g of benzyl 3(S)-2-[N-methyl-N-(2-ethoxycarbonylethyl)carbamoyl]-1,2,3,4-tetrahydroisoquinoline-3-carboxylate, 0.1 g of palladium-black and 59 ml of methanol is shaken in hydrogen gas atmosphere at room temperature under 3 atmospheric pressures for 4 hous. After the reaction, insoluble materials are removed by filtration, and the filtrate is evaporated under reduced pressure to remove solvent. 4.45 g of 3(S)-2-[N-methyl-N-(2-ethoxycarbonylethyl)-carbamoyl]-1,2,3,4-tetrahydroisoquinoline-3-carboxylic acid are thereby obtained as a colorless viscous oil.

Yield: 95.8%

IR$\nu_{max}^{film}$(cm$^{-1}$): 1735, 1635

4.45 g of the product obtained above are dissolved in 50 ml of methanol, and a solution of 1.85 g of L-lysine in 5 ml of water is added thereto. The mixture is condensed under reduced pressure to dryness. Ether is added to the residue, and the resultant crystals are collected by filtration. 5.45 g of 3(S)-2-[N-methyl-N-(2-ethoxycarbonylethyl)carbamoyl]-1,2,3,4-tetrahydroisoquinoline-3-carboxylic acid L-lysine salt are thereby obtained as colorless powder.

Yield: 85.2%

IR$\nu_{max}^{KBr}$(cm$^{-1}$): 1730, 1640 (broad), 1580 (broad)

$[\alpha]_D^{27}$ $+8.6°$ (C=1, water)

EXAMPLE 20

5.35 g of benzyl 3(S)-1,2,3,4-tetrahydroisoquinoline-3-carboxylate, 2.9 g of ethyl 3-ethylaminopropionate (B.p. 90° C./33 mm Hg), 3.0 g of phosgene, 5.4 g of triethylamine and 70 ml of methylene chloride are treated in the same manner as described in Example 18-(2). 5.4 g of benzyl 3(S)-2-[N-ethyl-N-(2-ethoxycabonylethyl)carbamoyl]-1,2,3,4-tetrahydroisoquinoline-3-carboxylate are thereby obtained as a colorless oil.

Yield: 61.5%

IR$\nu_{max}^{film}$(cm$^{-1}$): 1735, 1640

NMR (CDCl$_3$)$\delta$: 6.9–7.4(m, 9H, aromatic), 5.10(s, 2H, C$\underline{H}_2$—Ph), 4.89(t, 1H, >C$\underline{H}$—N), 4.53(s, 2H, Ar—C$\underline{H}_2$—N), 4.08(q, 2H, O—C$\underline{H}_2$CH$_3$), 3.0–3.8 (m, 6H, Ar—CH$_2$—C and —N—CH$_2$—), CH$_2$CH$_3$ 2.53 (t, 2H, C$\underline{H}_2$—CO), 1.21 (t, 3H, O-CH$_3$), 1.17 (t, 3H, N—CH$_2$C$\underline{H}_3$)

Mass m/e: 438 (M$^+$)

$[\alpha]_D^{27}$ $-3.0°$ (C=2, methanol)

EXAMPLE 21

3.0 g of phosgene are dissolved in 20 ml of methylene chloride, and a solution of 2.9 g of ethyl 3-ethylaminopropionate and 3.0 g of triethylamine in 20 ml of methylene chloride is added dropwise to the phosgene solution at $-30°$ to $-20°$ C. under stirring. The mixture is further stirred at the same temperature for 30 minutes. Then, the reaction mixture is condensed under reduced pressure to dryness. The residue (i.e., ethyl N-chlorocarbonyl-3-ethylaminopropionate) is dissolved in 20 ml of methylene chloride. A solution of 5.35 g of benzyl 3(S)-1,2,3,4-tetrahydroisoquinoline-3-carboxylate and 2.4 g of triethylamine in 10 ml of methylene chloride is added to the propionate solution at room temperature under stirring. The mixture is treated in the same manner as described in Example 18-(2). 4.6 g of benzyl 3(S)-2-[N-ethyl-N-(2-ethoxycarbonylethyl)carbamoyl]-1,2,3,4-tetrahydroisoquinoline-3-carboxylate are thereby obtained.

Yield: 52.4%

The physico-chemical poperties of this product are identical with those of the product obtained in Example 20.

EXAMPLE 22

A mixture of 4.39 g of benzyl 3(S)-2-[N-ethyl-N-(2-ethoxycarbonylethyl)carbamoyl]-1,2,3,4-tetrahydroisoquinoline-3-carboxylate, 80 mg of palladium-black and 44 ml of methanol is treated in the same manner as described in Example 19. 3.48 g of 3(S)-2-[N-ethyl-N-(2-ethoxycarbonylethyl)carbamoyl]-1,2,3,4-tetrahydroisoquinoline-3-carboxylic acid are thereby obtained as a colorless viscous oil.

Yield: theoretical

IR$\nu_{max}^{film}$(cm$^{-1}$): 1730, 1635

L-lysine salt:

IR$\nu_{max}^{KBr}$(cm$^{-1}$): 1735, 1640 (broad), 1570 (broad)

$[\alpha]_D^{27}$ $+3.9°$ C. (C=1, water)

Calcium salt:

M.p. 157°–161° C. (decomp.)

$[\alpha]_D^{23}$ $+11.7°$ (C=1, methanol)

Analysis calculated for C$_{36}$H$_{46}$N$_4$O$_{10}$Ca.$\frac{1}{2}$H$_2$O

C, 58.12; H, 6.37; N, 7.53;
Found: C, 58.10; H, 6.43; N, 7.54

EXAMPLE 23

5.35 g of benzyl 3(S)-1,2,3,4-tetrahydroisoquinoline-3-carboxylate, 3.5 g of n-butyl 3-ethylaminopropionate (B.p. 115° C./33 mmHg), 3.0 g of phosgene, 5.4 g of triethylamine and 70 ml of methylene chloride are treated in the same manner as described in Example 18-(2). 5.5 g of benzyl 3(S)-2-[N-ethyl-N-(2-n-butoxycarbonylethyl)carbamoyl]-1,2,3,4-tetrahydroisoquinoline-3-carboxylate are thereby obtained as a colorless oil.

Yield: 58.9%
IR$\nu_{max}^{film}$(cm$^{-1}$): 1730, 1640
NMR (CDCl$_3$)δ: 6.9–7.5(m, 9H, aromatic H), 5.14(s, 2H, C$\underline{H}_2$—Ph), 4.93(t, 1H, >C$\underline{H}$—N),
4.57(s, 2H, Ar—C$\underline{H}_2$—N), 4.06(t, 2H, —COOC$\underline{H}_2$—),

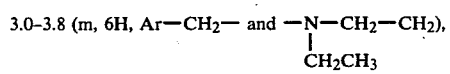

3.0–3.8 (m, 6H, Ar—CH$_2$— and —N—CH$_2$—CH$_2$),
 |
 CH$_2$CH$_3$ 2.46(t, 2H, C$\underline{H}_2$COO), 1.0–1.8(m, 4H, COOCH$_2$C$\underline{H}_2$C$\underline{H}_2$CH$_3$), 1.17(t, 3H, N—CH$_2$C$\underline{H}_3$), 0.89(t, 3H, C—CH$_2$C$\underline{H}_3$)
Mass m/e: 466 (M$^+$)
[α]$_D^{27}$ −2.6° (C=2, methanol)

EXAMPLE 24

A mixture of 5.0 g of benzyl 3(S)-2-[N-ethyl-N-(2-n-butoxycarbonylethyl)carbamoyl]-1,2,3,4-tetrahydroisoquinoline-3-carboxylate, 90 mg of palladium-black and 50 ml of methanol is treated in the same manner as described in Example 19. 3.7 g of 3(S)-2-[N-ethyl-N-(2-n-butoxycarbonylethyl)carbamoyl]-1,2,3,4-tetrahydroisoquinoline-3-carboxylic acid are thereby obtained as a colorless viscous oil. Yield: 97.9%

IR$\nu_{max}^{film}$(cm$^{-1}$): 1730, 1635
L-lysine salt:
IR$\nu_{max}^{KBr}$(cm$^{-1}$): 1730, 1640 (broad), 1570 (broad)
[α]$_D^{27}$ +4.7° (C=1, water)
Calcium salt:
M.p. 135°–136° C. (decomp.)
[α]$_D^{23}$ +11.0° (C=1, methanol)
Analysis calculated for C$_{40}$H$_{54}$N$_4$O$_{10}$Ca C, 60.74; H, 6.88; N, 7.08; Found, C, 60.76; H, 6.98; N, 7.15

EXAMPLE 25

(1) 8.6 g of methyl acrylate are added dropwise to 5.9 g of isopropylamine under ice-cooling and stirring. The mixture is further stirred at room temperature for 5 hours. Then, the reaction mixture is distilled under reduced pressure. 12.3 g of methyl 3-isopropylaminopropionate are thereby obtained as a colorless oil. Yield: 84.5%

B.p. 80°–81° C./29 mm Hg p (2) 5.35 g of benzyl 3(S)-1,2,3,4-tetrahydroisoquinoline-3-carboxylate, 2.9 g of methyl 3-isopropylaminopropionate, 3.0 g of phosgene, 5.4 g of triethylamine and 70 ml of methylene chloride are treated in the same manner as described in Example 18-(2). 4.6 g of benzyl 3(S)-2-[N-isopropyl-N-(2-methoxycarbonylethyl)carbamoyl]-1,2,3,4-tetrahydroisoquinoline-3-carboxylate are thereby obtained as a colorless oil.

Yield: 52.4%
IR$\nu_{max}^{film}$(cm$^{-1}$): 1740, 1640

NMR (CDCl$_3$)δ: 7.0–7.4(m, 9H, aromatic H), 5.09(s, 2H, CH$_2$Ph), 4.89(t, 1H, >C$\underline{H}$—N), 4.51(s, 2H, Ar—C$\underline{H}_2$—N), 3.5–4.0(m, 1H, —C$\underline{H}$(CH$_3$)$_2$), 3.57(s, 3H, OC$\underline{H}_3$), 3.26(t, 2H, N—C$\underline{H}_2$CH$_2$), 3.21(d, 2H, Ar—C$\underline{H}_2$—C), 2.45(t, 2H, C$\underline{H}_2$—COO), 1.20(d, 3H, CH—C$\underline{H}_3$), 1.09(d, 3H, >CH—C$\underline{H}_3$)
Mass m/e: 438 (M$^+$)

EXAMPLE 26

A mixture of 3.8 g of benzyl 3(S)-2-[N-isopropyl-N-(2-methoxycarbonylethyl)carbamoyl]-1,2,3,4-tetrahydroisoquinoline-3-carboxylate, 80 mg of palladium-black and 38 ml of methanol is treated in the same manner as described in Example 19. 2.8 g of 3(S)-2-[N-isopropyl-N-(2-methoxycarbonylethyl)carbamoyl]-1,2,3,4-tetrahydroisoquinoline-3-carboxylic acid are thereby obtained as a colorless viscous oil. Yield: 92.7%

IR$\nu_{max}^{film}$(cm$^{-1}$): 1740, 1640
L-lysine salt:
colorless powder
IR$\nu_{max}^{KBr}$(cm$^{-1}$): 1735, 1630 (broad), 1570 (broad)
[α]$_D^{27}$ −0.7° (C=1, water)
Sodium salt:

0.41 g of sodium bicarbonate and 20 ml of water are added to 1.7 g of 3(S)-2-[N-isopropyl-N-(2-methoxycarbonylethyl)carbamoyl]1,2,3,4-tetrahydroisoquinoline-3-carboxylic acid, and the mixture is stirred at room temperature for 30 minutes. Then, the reaction mixture is condensed under reduced pressure to dryness. Ether is added to the residue, and the precipitates are collected by filtration. 1.7 g of 3(S)-2-[N-isopropyl-N-(2-methoxycarbonylethyl)carbamoyl]-1,2,3,4-tetrahydroisoquinoline-3-carboxylic acid sodium salt are thereby obtained as colorless powder. Yield 93.9%

IR$\nu_{max}^{KBr}$(Cm$^{-1}$): 1735, 1620 - 1590
[α]$_D^{27}$ −1.6° (C=1, water)

EXAMPLE 27

5.35 g of benzyl 3(S)-1,2,3,4-tetrahydroisoquinoline-3-carboxylate, 3.2 g of ethyl 3-isopropylaminopropionate (B.p. 91°–92° C./23 mm Hg), 3.0 g of phosgene, 5.4 g of triethylamine and 70 ml of methylene chloride are treated in the same manner as described in Example 18-(2). 5.3 g of benzyl 3(S)-2-[N-isopropyl-N-(2-ethoxycarbonylethyl)carbamoyl]-1,2,3,4-tetrahydroisoquinoline-3-carboxylate are thereby obtained as a colorless oil.

Yield: 58.5%
IR$\nu_{max}^{film}$(cm$^{-1}$): 1730, 1640
NMR (CDCl$_3$)δ: 6.9–7.5(m, 9H, aromatic H), 5.12(s, 2H, —C$\underline{H}_2$Ph), 4.92(t, 1H, >C$\underline{H}$—N), 4.54(s, 2H, Ar—C$\underline{H}_2$—N), 3.4–4.1 (m, 1H, C$\underline{H}$(CH$_3$)$_2$), 3.28( t, 2H, N—C$\underline{H}_2$CH$_2$), 3.23(d, 2H, Ar—C$\underline{H}_2$—C), 2.46(t, 2H, CH$_2$—COO),

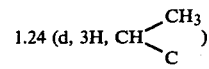

1.17(t, 3H, C$\underline{H}_2$CH$_3$),

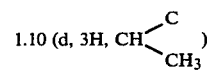

Mass m/e: 452 (M$^+$)
[α]$_D^{27}$ −4.3° (C=2, methanol)

EXAMPLE 28

A mixture of 4.5 g of benzyl 3(S)-2-[N-isopropyl-N-(2-ethoxycarbonylethyl)carbamoyl]-1,2,3,4-tetrahydroisoquinoline-3-carboxylate, 80 mg of palladium-black and 45 ml of methanol is treated in the same manner as described in Example 19. 3.4 g of 3(S)-2-[N-isopropyl-N-(2-ethoxycarbonylethyl)-carbamoyl]-1,2,3,4-tetrahydroisoquinoline-3-carboxylic acid are thereby obtained as a colorless viscous oil.

Yield: 94.4%
IR$\nu_{max}^{film}$(cm$^{-1}$): 1735, 1640
L-lysine salt:
  colorless powder
  IR$\nu_{max}^{KBr}$(cm$^{-1}$): 1730, 1640 (broad), 1570 (broad)
  $[\alpha]_D^{27} -2.3°$ (C=1, water)

EXAMPLE 29

(1) 27.8 g of n-butyl acrylate are added dropwise to 15.6 g of isopropylamine under ice-cooling and stirring. The mixture is further stirred at room temperature for 5 hours. Then, the reaction mixture is distilled under reduced pressure. 33 g of n-butyl 3-isopropylaminopropionate are thereby obtained as a colorless oil.

Yield: 80%
B.p. 126°–127° C./33 mm Hg
IR$\nu_{max}^{film}$(cm$^{-1}$): 3220, 1740

(2) 5.35 g of benzyl 3(S)-1,2,3,4-tetrahydroisoquinoline-3-carboxylate, 3.75 g of n-butyl 3-isopropylaminopropionate, 3.0 g of phosgene, 5.4 g of triethylamine and 70 ml of methylene chloride are treated in the same manner as described in Example 18-(2). 4.6 g of benzyl 3(S)-2-[N-isopropyl-N-(2-n-butoxycarbonylethyl)carbamoyl]-1,2,3,4-tetrahydroisoquinoline-3-carboxylate are thereby obtained as a colorless oil.

Yield: 47.9%.
IR$\nu_{max}^{film}$(cm$^{-1}$): 1735, 1640
NMR (CDCl$_3$)δ: 6.9–7.4 (m, 9H, aromatic H), 5.09 (s, 2H, —C$\underline{H}_2$—Ph), 4.92 (t, 1H, >C$\underline{H}$—N), 4.52 (s, 2H, Ar—C$\underline{H}_2$—N), 3.98 (t, 2H, COOC$\underline{H}_2$), 3.4–4.1 (m, 1H, —C$\underline{H}$(CH$_3$)$_2$), 3.26 (t, 2H, N—C$\underline{H}_2$), 3.22 (d, 2H, Ar—C$\underline{H}_2$—C), 2.46 (t, 2H, C$\underline{H}_2$—COO), 1.1–1.7 (m, 4H, COOCH$_2$C$\underline{H}_2$C$\underline{H}_2$CH$_3$),

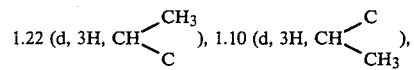

0.89 (t, 3H, CH$_2$—C$\underline{H}_3$)
Mass m/e: 480 (M$^+$)
$[\alpha]_D^{27} -4.2°$ (C=2, methanol)

EXAMPLE 30

A mixture of 2.4 g of benzyl 3(S)-2-[N-isopropyl-N-(2-n-butoxycarbonylethyl)carbamoyl]-1,2,3,4-tetrahydroisoquinoline-3-carboxylate, 60 mg of palladium-black and 24 ml of methanol is treated in the same manner as described in Example 19. 1.9 g of 3(S)-2-[N-isopropyl-N-(2-n-butoxycarbonylethyl)-carbamoyl]-1,2,3,4-tetrahydroisoquinoline-3-carboxylic acid are thereby obtained as a colorless viscous oil.

Yield: 97.4%
IR$\nu_{max}^{film}$(cm$^{-1}$): 1730, 1635
L-lysine salt:
  colorless powder
  IR$\nu_{max}^{KBr}$(cm$^{-1}$): 1735, 1640 (broad), 1570 (broad)
  $[\alpha]_D^{27} -1.7°$ (C=1, water)

EXAMPLE 31

4.1 g of ethyl 3(S)-1,2,3,4-tetrahydroisoquinoline-3-carboxylate, 2.62 g of ethyl 3-methylaminopropionate, 3.0 g of phosgene, 5.4 of triethylamine and 50 ml of methylene chloride are treated in the same manner as described in Example 3. 5.3 g of ethyl 3(S)-2-[N-methyl-N-(2-ethoxycarbonylethyl)carbamoyl]-1,2,3,4-tetrahydroisoquinoline-3-carboxylate are thereby obtained as a colorless viscous oil.

Yield: 73.1%
IR$\nu_{max}^{film}$(cm$^{-1}$): 1735, 1640
NMR (CDCl$_3$)δ: 4.10 (q, 2H×2, O—C$\underline{H}_2$—CH$_3$), 2.95 (s, 3H, N—C$\underline{H}_3$), 1.21 (t, 3H, O—CH$_2$—C$\underline{H}_3$), 1.18 (t, 3H, O—CH$_2$—C$\underline{H}_3$)
Mass m/e: 362 (M$^+$)
$[\alpha]_D^{26} +4.5°$ (C=2, methanol)

EXAMPLE 32

3.5 g of t-butyl 3(S)-1,2,3,4-tetrahydroisoquinoline-3-carboxylate, 2.0 g of methyl 3-ethylaminopropionate, 2.25 g of phosgene, 4.1 g of triethylamine and 50 of methylene chloride are treated in the same manner as described in Example 3. 3.9 g of t-butyl 3(S)-2-[N-ethyl-N-(2-methoxycarbonylethyl)carbamoyl]-1,2,3,4-tetrahydroisoquinoline-3-carboxylate are thereby obtained as a colorless viscous oil.

Yield: 66.6%
IR$\nu_{max}^{film}$(cm$^{-1}$): 1740, 1645
NMR (CDCl$_3$)δ: 3.62 (s, 3H, O—CH$_3$),

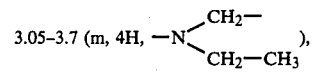

1.32 (s, 3H×3, C(CH$_3$)$_3$), 1.20 (t, 3H, N—CH$_2$—C$\underline{H}_3$)
Mass m/e: 390 (M$^+$)

EXAMPLE 33

4.1 g of ethyl 3(S)-1,2,3,4-tetrahydroisoquinoline-3-carboxylate, 2.9 g of ethyl 3-ethylaminopropionate, 3.0 g of phosgene, 5.4 g of triethylamine and 50 ml of methylene chloride are treated in the same manner as described in Example 3. 5.6 g of ethyl 3(S)-2-[N-ethyl-N-(2-ethoxycarbonylethyl)carbamoyl]-1,2,3,4-tetrahydroisoquinoline-3-carboxylate are thereby obtained as a colorless viscous oil.

Yield: 74.4%
IR$\nu_{max}^{film}$(cm$^{-1}$): 1740, 1640
NMR (CDCl$_3$)δ: 4.09 (q, 2H×2, O—C$\underline{H}_2$CH$_3$), 3.48 (q, 2H, N—C$\underline{H}_2$—CH$_3$), 1.21 (t, 3H×2, O—CH$_2$—C$\underline{H}_3$), 1.18 (t, 3H, N—CH$_2$—C$\underline{H}_3$)
Mass m/e: 376 (M$^+$)
$[\alpha]_D^{26} -0.2°$ (C=2, methanol)

EXAMPLE 34

4.1 g of ethyl 3(S)-1,2,3,4-tetrahydroisoquinoline-3-carboxylate, 3.2 g of ethyl 3-isopropylaminopropionate, 3.0 g of phosgene, 5.4 g of triethylamine and 50 ml of methylene chloride are treated in the same manner as described in Example 3. 5.6 g of ethyl 3(S)-2-[N-isopropyl-N-(2-ethoxycarbonylethyl)carbamoyl]-1,2,3,4-tetrahydroisoquinoline-3-carboxylate are thereby obtained as a colorless viscous oil.

Yield: 71.7%
IR$\nu_{max}^{film}$(cm$^{-1}$): 1740, 1645

NMR (CDCl₃)δ: 4.10 (q, 2H, O—C$\underline{H}_2$—CH₃), 4.05 (q, 2H, O—C$\underline{H}_2$—CH₃), 3.9-4.3 (m, 1H, C$\underline{H}$(CH₃)₂), 1.0-1.5 (m, 12H, O—CH₂C$\underline{H}_3$×2, CH(C$\underline{H}_3$)₂)

Mass m/e: 390 (M⁺)

$[\alpha]_D^{26}$ −4.6° (C=2, methanol)

EXAMPLE 35

4.1 g of ethyl 3(S)-1,2,3,4-tetrahydroisoquinoline-3-carboxylate, 3.46 g of isopropyl 3-isopropylaminopropionate, 3.0 g of phosgene, 5.4 g of triethylamine and 50 ml of methylene chloride are treated in the same manner as described in Example 3. 6.3 g of ethyl 3(S)-2-[N-isopropyl-N-(2-isopropoxycarbonylethyl)carbamoyl]-1,2,3,4-tetrahydroisoquinoline-3-carboxylate are thereby obtained as a colorless viscous oil.

Yield: 77.9%

IR$\nu_{max}^{film}$(cm⁻¹): 1730, 1645

NMR (CDCl₃)δ: 4.8-4.2 (m, 1H, O—C$\underline{H}$(CH₃)₂), 4.10 (q, 2H, O—C$\underline{H}_2$—CH₃), 3.7-4.15 (m, 1H, N—C$\underline{H}$(CH₃)₂), 1.18 (d, 6H, >CH—C$\underline{H}_3$×2), 1.16 (d, 6H, >CH—C$\underline{H}_3$×2), 1.16 (t, 3H, O—CH₂—C$\underline{H}_3$)

Mass m/e: 404 (M⁺)

$[\alpha]_D^{26}$ −5.0° (C=2, methanol)

EXAMPLE 36

4.1 of ethyl 3(S)-1,2,3,4-tetrahydroisoquinoline-3-carboxylate, 3.72 g of n-butyl 3-isopropylaminopropionate, 3.0 g of phosgene, 5.4 g of triethylamine and 50 ml of methylene chloride are treated in the same manner as described in Example 3. 6.1 g of ethyl 3(S)-2-[N-isopropyl-N-(2-n-butoxycarbonylethyl)carbamoyl]-1,2,3,4-tetrahydroisoquinoline-3-carboxylate are thereby obtained as a colorless viscous oil.

Yield: 72.9%

IR$\nu_{max}^{film}$(cm⁻¹): 1740, 1640

NMR (CDCl₃)δ: 4.11 (q, 2H, O—C$\underline{H}_2$—CH₃), 4.00 (t, 2H, O—C$\underline{H}_2$—CH₂), 3.9-4.2 (m, 1H, C$\underline{H}$(CH₃)₂), 1.2-1.8 (m, 4H, O—CH₂—C$\underline{H}_2$—C$\underline{H}_2$—), 1.26 (d, 3H, >CH—C$\underline{H}_3$), 1.18 (t, 3H, O—CH₂—C$\underline{H}_3$), 1.16 (d, 3H, CH—C$\underline{H}_3$), 0.89 (t, 3H, C—CH₂—C$\underline{H}_3$)

Mass m/e: 418 (M⁺)

$[\alpha]_D^{26}$ −4.1° (C=2, methanol)

EXAMPLE 37

3.8 g of methyl 3(S)-1,2,3,4-tetrahydroisoquinoline-3-carboxylate, 3.74 g of triethylamine and 50 ml of methylene chloride are treated in the same manner as described in Example 3. 5.2 g of methyl 3(S)-2-[N-isopropyl-N-(2-t-butoxycarbonylethyl)carbamoyl]-1,2,3,4-tetrahydroisoquinoline-3-carboxylate are thereby obtained as a colorless viscous oil.

Yield: 64.3%

IR$\nu_{max}^{film}$(cm⁻¹): 1730, 1645

NMR (CDCl₃)δ: 3.6-4.1 (m, 1H, C$\underline{H}$(CH₃)₂), 3.7 (s, 3H, O—C$\underline{H}_3$), 1.42 (s, 3H×3, C(C$\underline{H}_3$)C₃), 1.19 (d, 3H×2, CH(C$\underline{H}_3$)₂)

Mass m/e: 404

EXAMPLE 38

4.1 g of ethyl 3(S)-1,2,3,4-tetrahydroisoquinoline-3-carboxylate, 3.1 g of ethyl 3-propargylaminopropionate, 3.0 g of phosgene, 5.4 of triethylamine and 50 ml of methylene chloride are treated in the same manner as described in Example 3. 5.6 g of ethyl 3(S)-2-[N-propargyl-N-(2-ethoxycarbonylethyl)carbamoyl]-1,2,3,4-tetrahydroisoquinoline-3-carboxylate are thereby obtained as a colorless viscous oil.

Yield: 72.5%

IR$\nu_{max}^{film}$(cm⁻¹): 3300, 1740, 1650

NMR (CDCl₃)δ: 3.8-4.3 (m, 2H, N—C$\underline{H}_2$—C≡C), 4.14 (q, 2H×2, O—C$\underline{H}_2$—CH₃), 2.3-2.4 (m, 1H, —C≡C$\underline{H}$), 1.20 (t, 3H, CH₂—C$\underline{H}_3$), 1.25 (t, 3H, CH₂—C$\underline{H}_3$)

Mass m/e: 386 (M⁺)

$[\alpha_D^{26}$ +1.7° (C=2, methanol)

What we claim is:

1. A tetrahydroisoquinoline compound of the formula:

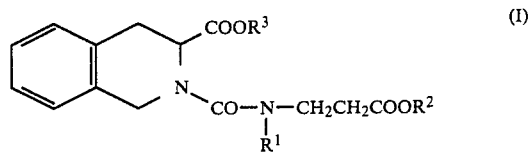

wherein R¹ is alkyl of one to six carbon atoms, cycloalkyl of three to six carbon atoms, allyl or propargyl, R² is hydrogen or alkyl of one to six carbon atoms, and R³ is hyrodgen, alkyl of one to six carbon atoms or benzyl, or a pharmaceutically acceptable salt thereof.

2. The compound of claim 1, in which R³ is hydrogen.

3. The compound of claim 2, in which R² is hydrogen.

4. The compound of claim 2, in which R² is alkyl of one to six carbon atoms.

5. The compound of claim 3, in which R¹ is alkyl of one to four carbon atoms, cyclopropyl, allyl or propargyl.

6. The compound of claim 4, in which R¹ is alkyl of one to four carbon atoms, cyclopropyl, allyl or propargyl, and R² is alkyl of one to four carbon atoms.

7. The compound of claim 5, in which R¹ is alkyl of one to four carbon atoms.

8. The compound of claim 5, in which R¹ is cyclopropyl, allyl or propargyl.

9. The compound of claim 6, in which R¹ is alkyl of one to four carbon atoms.

10. The compound of claim 7 which is 3(S)-2-[N-ethyl-N-(2-carboxyethyl)carbamoyl]-1,2,3,4-tetrahydroisoquinoline-3-carboxylic acid or a pharmaceutically acceptable salt thereof.

11. The compound of claim 7 which is 3(S)-2-[N-isopropyl-N-(2-carboxyethyl)carbamoyl]-1,2,3,4-tetrahydroisoquinoline-3-carboxylic acid or a pharmaceutically acceptable salt thereof.

12. The compound of claim 8 which is 3(S)-2-([N-propargyl-N-(2-carboxyethyl)carbamoyl]-1,2,3,4-tetrahydro-isoquinoline-3-carboxylic acid or pharmaceutically acceptable salt thereof.

13. The compound of claim 9 which is 3(S)-2-[N-ethyl-N-(2-ethoxycarbonylethyl)carbamoyl]-1,2,3,4-tetrahydroisoquinoline-3-carboxylic acid or a pharmaceutically acceptable salt thereof.

14. The compound of claim 9 which is 3(S)-2-[N-ethyl-N-(2-n-butoxycarbonylethyl)carbamoyl]-1,2,3,4-tetrahydroisoquinoline-3-carboxylic acid or a pharmaceutically acceptable salt thereof.

15. The compound of claim 9 which is 3(S)-2-[N-isopropyl-N-(2-ethyoxycarbonylethyl)carbamoyl]-1,2,3,4-tetrahydroisoquinoline-3-carboxylic acid or a pharmaceutically acceptable salt thereof.

16. The compound of claim 9 which is 3(S)-2-[N-isopropyl-N-(2-n-butoxycarbonylethyl)carbamoyl]-

1,2,3,4-tetrahydroisoquinoline-3-carboxylic acid or a pharmaceutically acceptable salt thereof.

17. An inhibitory composition for the treatment of angiotensin-related hypertension comprising an amount of the compound of claim 1 such that, when said composition is administered to a warm blooded animal, it will provide an effective amount in said animal, and a pharmaceutically acceptable carrier therefor.

* * * * *